United States Patent [19]

Hoshino et al.

[11] Patent Number: 5,312,561

[45] Date of Patent: May 17, 1994

[54] DETERGENT COMPOSITION

[75] Inventors: Eiichi Hoshino; Kazuo Mori, both of Wakayama; Akira Suzuki; Jun Hitomi, both of Takanezawamachi, all of Japan

[73] Assignee: Kao Corporation, Tokyo, Japan

[21] Appl. No.: 823,360

[22] Filed: Jan. 21, 1992

[30] Foreign Application Priority Data

Jan. 22, 1991 [JP] Japan ................................ 3-021565
Feb. 28, 1991 [JP] Japan ................................ 3-034396
Dec. 10, 1991 [JP] Japan ................................ 3-325980

[51] Int. Cl.$^5$ ............................................ C11D 3/386
[52] U.S. Cl. ........................ 252/174.12; 252/DIG. 12
[58] Field of Search ................... 252/171.42, DIG. 12, 252/174.12

[56] References Cited

U.S. PATENT DOCUMENTS 4,052,262 10/1977 Horikoshi et al. ............ 252/DIG. 12
4,797,362 1/1989 Takeuchi et al. ..................... 435/221

FOREIGN PATENT DOCUMENTS 0204342 12/1986 European Pat. Off. .
1-074986 3/1989 Japan .
1-101885 4/1989 Japan .

OTHER PUBLICATIONS

Tsai, Y-C, et al., "Characterization of an Alkaline Protease from Alkalophilic Bacillus YA-B", Biochim Biophys Acta, vol. 883, No. 3, 1986, pp. 439-447. month unknown.

Takami, H., et al, "Characterization of an Alkaline Protease from Bacillus SP No. AH-101", Appl. Microbiol. Biotechnol., vol. 3, No. 5, 1990, pp. 519-523. month unknown.

Primary Examiner—Olik Chaudhuri
Assistant Examiner—C. Everhart
Attorney, Agent, or Firm—Oblon, Spivak, McClelland, Maier & Neustadt

[57] ABSTRACT

A detergent compositions comprising an alkaline protease, having an optimum pH range on the alkaline side, having an activity of hydrolyzing human horny keratin fiber of 40 KFU/APU or more, possessing a superior activity toward insoluble proteins, and exhibiting a sufficient activity in a wide temperature range, exhibit excellent detergency toward protein soils.

3 Claims, 8 Drawing Sheets

DETERGENT COMPOSITION

BACKGROUND OF THE INVENTION

1. Field of the Invention

The present invention relates to detergent compositions, and, more particularly, to detergent compositions exhibiting an excellent detergency against protein soil. The present invention also relates to alkaline proteases which exhibit a high activity for hydrolyzing human horny keratin fiber and microorganisms which produce such proteases.

2. Description of the Background

Conventionally, various proteases have been incorporated into detergents for washing clothes and detergents for automated dish-washing machines in order to remove protein soil. Alkaline proteases exhibiting their activities in an alkaline region are used for such proteases.. Typical examples of such alkaline proteases are Alcalase, Savinase (a product of Novo Nordisk Co.), API-21 (Showa Denko Co., Ltd.), Maxacal (Gist Brocades Co.), and the like. Problems with many of these alkaline proteases have been their insufficient detergency against insoluble protein soils in such portions of clothes as collars, sleeves, and the like. Detergent compositions in which these alkaline proteases are incorporated do not exhibit sufficient detergency against protein soils.

Ya enzyme is reported (Japanese Patent Laid-open (kokai) No. 280278/1986) to be stable against surface active agents. This enzyme, however, is active on the high temperature range, and therefore generally is not suitable for use as a detergent to be used around room temperature.

Thus, there remains a need for detergent composition with a superior capability of removing protein soils, using an alkaline protease which is highly stable in surfactant solutions, active in a wide temperature range, and active for insoluble proteins.

SUMMARY OF THE INVENTION

Accordingly, it is ah object of the present invention to provide novel detergent compositions which exhibit excellent detergency against water-insoluble proteins.

It is another object of the present invention to provide detergent compositions comprising an alkaline protease having 40 KFU/APU or more of activity of hydrolyzing human horny keratin fiber.

It is another object of the present invention to provide novel alkaline proteases which have 40 KFU/APU or more of activity of hydrolyzing human horny keratin fiber.

It is another object of the present invention to provide novel microorganisms which produce such proteases.

These and other objects, features and advantages of the present invention, which will become more readily apparent from the following detailed description, have been achieved by the inventors' discovery that detergent compositions with a superior detergency against protein soils, especially insoluble protein soils in collars and sleeves, could be produced by incorporating an alkaline protease possessing a superior capability of hydrolyzing insoluble proteins, especially human horny keratin fiber and by the inventors' discovery of microorganisms which produce such proteases. This finding has led to the completion of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Alkaline proteases suitable for use in the present invention have an activity of hydrolyzing human horny keratin fiber of 40 KFU/APU or more. Here, the activity of hydrolyzing human horny keratin fiber designates a ratio of the hydrolyzing power of protease for human horny keratin fiber (KFU) to that of the same protease for urea-denatured hemoglobin (APU) which is a water-soluble protein. It can be measured by the method hereinafter described.

In the present invention, an alkaline protease means an enzyme which is stable and exhibits a protease activity under alkaline conditions. Particularly preferable are alkaline proteases having an optimum pH and an optimum temperature in the following ranges.

(1) Optimum pH (Measured using casein as substrate at 40° C. for 10 minutes): 10.0–12.5

(2) Optimum temperature (Measured using casein as substrate at pH 10.0, $Ca^{2+}$ not added) 50°–60° C.

There are no specific restrictions as to alkaline proteases used in the present invention so long as they satisfy the above requirements. Alkaline proteases K-16 and K-14 are given as specific examples.

Alkaline proteases K-16 and K-14 used in the present invention can be prepared by cultivating microorganisms belonging to genus Bacillus and collecting the enzymes from the culture broth. Microorganisms having the following mycological characteristics are given as examples of such microorganisms.

Microorganism Producing Alkaline Protease K-16

(A) Morphological characteristics
  (a) Shape and size of cells: rods, 0.8–1.0 $\mu m \times 2.2$–25 $\mu m$
  (b) Polymorphism: None
  (c) Motility: Cells possess paritrichous flagella and motile.
  (d) Spores (size, shape, site): 1.0–1.2 $\mu m \times 1.4$–2.2 $\mu m$, elliptical, central to subterminal; slightly swollen sporangium.
  (e) Gram's staining: positive
  (f) Acid fastness: negative (g) Growth on nutrient agar plate: light yellow and transparent colony with a circular erose.
(h) Growth on nutrient agar slant culture: Colony is light yellow and semitransparent with an irregular erose shape and a slightly rough surface.
(i) Culture in nutrient broth: Cells grow well, the broth is cloudy with no pellicle.
(j) Stab culturing in nutrient gelatin: Cells grow well; liquefaction of gelatin is accompanied.
(k) Litmus milk: Peptonization occurs, with no coagulation of milk. No color change occurs.

(B) Physiological characteristics
  (a) Nitrate reduction: Positive
  (b) Denitrification: Negative
  (c) MR test: Negative
  (d) V-P test: Positive
  (e) Production of indole: Negative
  (f) Production of hydrogen sulfide: Negative
  (g) Hydrolysis of starch: Positive
  (h) Utilization of citric acid: Positive
  (i) Utilization of inorganic nitrogen sources: Utilize sodium nitrate, but not ammonium salts
  (j) Pigment production: Negative
  (k) Urease: Negative
  (l) Oxidase: Positive
  (m) Catalase: Positive
  (n) Growth temperature range: Below 55° C.
  (o) Growth pH range: Can grow at pH 6.6–10.3
  (p) Behavior on oxygen: Aerobic
  (q) O-F test: Oxidation (O)
  (r) Resistance to sodium chloride: Can grow under 10% sodium chloride
  (s) Acid or gas production from sugar: Produces no gas from any sugars.

TABLE 1

| (Acid production from sugars) | |
|---|---|
| Sugars | Acid production |
| D-Ribose | + |
| L-Arabinose | + |
| D-Xylose | + |
| D-Fructose | + |
| D-Glucose | + |
| D-Mannose | + |
| D-Galactose | + |
| Maltose | + |
| Sucrose | + |
| Lactose | + |
| Trehalose | + |
| Starch | + |
| Sorbitol | + |
| Inositol | − |
| Mannitol | + |
| Glycerol | + |
| Dextrin | + |
| Raffinose | + |

Based on the above morphological and taxonomic characteristics, the microorganism of the present invention was examined referring to Bergey's Manual of Systematic Bacteriology (Williams & Wilkins Co., 1986) and was considered to belong to the genus *Bacillus subtilis*. However, there are differences between *Bacillus subtilis* and the microorganism of the present invention in that while the former cannot grow at pH 10, pH 10, the latter can grow well at pH 10, and further while *Bacillus subtilis* cannot grow at 55° C., the microorganism of the present invention can grow at 55° C.

From the above facts, notwithstanding the good reasons to speculate that the microorganism of the present invention belongs to *Bacillus subtilis*, it was judged to be another novel microorganism due to several differences in their characteristics and also due to the differences from any other known microorganisms.

Thus, in another embodiment, the present invention relates to the novel microorganism named Bacillus sp. KSM-K16 possessing the properties described above, and has been deposited with the Fermentation Research Institute, Agency of Industrial Science and Technology as FERM BP-3376.

The microorganisms K-16 and KSM-K-16 are described in Japanese Patent Applications 3-33117 and 3-33116, respectively, and in U.S. patent application Ser. No. 07/816,243 which is incorporated herein by reference.

Microorganism Producing Alkaline Proteinase K-14

(A) Morphological characteristics
  (a) Shape and size of cells: rods, 0.8–1.0 $\mu$m × 2.5–25.5 $\mu$m
  (b) Polymorphism: None
  (c) motility: Cells possess peritrichous flagella and mitile.
  (d) Spores (size, shape, site): 1.0–1.2 $\mu$m × 1.5–2.2 $\mu$m, elliptical, central to subterminal; slightly swollen sporangium.
  (e) Gram's staining: positive
  (f) Acid fastness: negative (B) Physiological characteristics
  (a) Nitrate reduction: Positive
  (b) Denitrification: Negative
  (c) MR test: Negative
  (d) V-P test: Positive
  (e) Production of indole: Negative
  (f) Production of hydrogen sulfide: Negative
  (g) Hydrolysis of starch: Positive
  (h) Utilization of citric acid: Positive
  (i) Utilization of inorganic nitrogen sources: Utilize sodium nitrate, but not ammonium salts
  (j) Pigment production: Negative
  (k) Urease: Negative
  (l) Oxidase: Positive
  (m) Catalase: Positive
  (n) Growth temperature range: Below 55° C.
  (o) Growth pH range: Can grow at pH 6.6–10.3
  (p) Behavior on oxygen: Aerobic
  (q) O-F test: Oxidation (O)
  (r) Resistance to sodium chloride: Can grow under 10% sodium chloride
  (s) Acid or gas production from sugar: Produces no gas from any sugars.

TABLE 2

| (Acid production from sugars) | |
|---|---|
| Sugars | Acid production |
| L-Arabinose | + |
| D-Xylose | + |
| D-Glucose | + |
| Mannitol | + |

Based on the above morphological and taxonomic characteristics, the microorganism of the present invention was examined referring to Bergey's Manual of Systematic Bacteriology (Williams & Wilkins Co., 1986) and was considered to belong to the genus *Bacillus subtilis*. However, there are differences between *Bacillus subtilis* and the microorganism of the present invention in that while the former cannot grow at pH 10, the latter can well grow at pH 10, and further that while *Bacillus subtilis* cannot grow at 55° C., the microorganism of the present invention can grow at 55° C.

From the above facts, notwithstanding the good reasons to speculate that the microorganism of the present invention belongs to *Bacillus subtilis*, it was judged to be another, novel microorganism due to several differences in their characteristics and also due to the differences from any other known microorganisms.

Thus, in another embodiment, the present invention relates to the novel microorganism named Bacillus sp. KSM-K14 possessing the properties described above, and has been deposited with the Fermentation Research Institute, Agency of Industrial Science and Technology as F(RM BP-3670.

In order to produce alkaline protease K-16 and/or K-14 of the present invention, these microorganisms are inoculated and cultivated in a suitable medium according to any conventional manner.

Any media which are used for the cultivation of common microorganisms and in which the microorganism of the present invention can grow may be used for the cultivation. It is desirable to add a suitable amount of carbon and nitrogen sources which the microorganism can utilize in the medium.

There are no specific limitations as to the carbon and nitrogen sources. Enumerated as examples of nitrogen sources are corn gluten meal, soybean flour, corn steep liquor, casamino acid, yeast extract, pharma media, sardine meal, meat extract, peptone, HYPRO ®, (Traeers), AJIPOWER ® (Kyowa Hakko), corn meal, soybean meal, coffee grounds, cotton seed grounds, CULTIVATOR ® (Yaizu Suisan K.K.), AMIFLEX ® (Takeda Chemical Industries, Ltd.), AJIPRON ® (Ajinomoto K.K.), ZYEST ® (Takeda Chemical Industries, Ltd.), AJIX ® and the like; and as carbon sources are arabinose, xylose, glucose, mannose, fructose, galactose, sucrose, maltose, lactose, sorbitol, mannitol, inositol, glycerol, soluble starch, inexpensive waste molasses, invert sugars, as well as utilizable organic acids such as acetic acid and the like. In addition to these carbon and nitrogen sources, phosphoric acid, inorganic salts of ions such as $Mg^{2+}$, $Ca^{2+}$, $Mn^{2+}$, $Zn^{2+}$, $Co^{2+}$, $Na^+$, $K^+$, etc., as well as trace amounts of other organic or inorganic nutrients, may be added as required.

Collection and purification of target alkaline protease K-16 or K-14 from the culture broth thus-prepared can be performed according to conventional methods applicable to the collection and purification of common enzymes.

Specifically, cells are separated from the culture broth by centrifugation, filtration, or the like; and the target alkaline proteinase can be separated and concentrated from the cells and the filtrate by a conventional separation means such as salting out, isoelectric precipitation, solvent precipitation, e.g., precipitation from methanol, ethanol, isopropyl alcohol, acetone, or the like; ultrafiltration, e.g., using Dia-flow membrane YC ® (a product of-Amicon Co.), and the like. It is possible to produce a lyophilized powder of the enzyme by collecting the enzyme by salting out using, for example, ammonium sulfate (30–70% saturation fraction), or by solvent precipitation from, for example, 75% ethanol, followed by filtration or centrifugation, and desalting. A conventional method such as dialysis or gel filtration using Sephadex G-25 ® (a product of Pharmacia) can be employed for the desalting.

Although it is possible to use the crude enzyme liquid thus obtained as is, the enzyme can also be used after purification and crystallization, as required. Such purification can be carried out by a suitable combination of fractionation means, such as, for example, adsorption chromatography, e.g., hydroxyapatite chromatography, ion-exchange chromatography, e.g, DEAE-SEPHADEX ® (Pharmacia), DEAE-Cellulose, or CM-Bio-Gel; or gel filtration chromatography, e.g., Sephadex or Bio-Gel.

Alkaline proteases K-16 and K-14 thus obtained have the following enzymological characteristics. Enzymatic activities discussed herein were measured by the following methods.

Casein Hydrolyzing Activity

A 1% solution of casein in 50 mM borate-NaOH buffer (pH 10.0, 1 ml) was mixed with 0.1 ml of an enzyme solution and incubated at 40° C. for 10 minutes. After the addition of a reaction termination solution (0.123 M trichloroacetic acid–0.246 M sodium acetate–0.369 M acetic acid), the mixture was allowed to stand at 30° C. for 20 minutes and filtered by No. 2 filter (made by Wattman Co.). Protein decomposition products in filtrate was measured by the modified Folin-Lowry method. One unit (P.U.) of enzymatic activity was defined as the amount of enzyme that released acid soluble amino acid or peptide equivalent to 1 mmol of tyrosine per minute under the above reaction conditions.

ACTIVITY OF HYDROLYZING HUMAN HORNY KERATIN FIBER (1) hydrolyzing power for urea-denatured hemoglobin A modified Anson-Hemoglobin method [M. L. Anson, *J. Gen. Physiol.*, 22, 79 (1938)] was used, in which a solution containing a substrate, urea-denatured hemoglobin, which final concentration being adjusted to 14.7 mg/ml, was reacted with enzyme at 25° C., pH 10.5 for 10 minutes. To the reaction mixture, trichloroacetic acid was added to have a final concentration of 31.25 mg/ml. Trichloroacetic acid-soluble protein was subjected to a color reaction with a phenol reagent. Activity per 10 minute reaction was first obtained (calibration curve: 1 APU=color provided with 1 mmol tyrosine), and this was converted into activity per 1 minute reaction. Namely, 1 APU indicates the amount of protease which provides a trichloroacetic acid-soluble protein in such amount that the protein amount per minute yields the same color degree as 1 mmol tyrosine yields with phenol.

(2) Hydrolyzing power for human horny keratin fiber (2-1) Preparation of keratin fiber Human heel epidermis (horny layer) cut by scalpel was fragmented with scissors and washed with ion-exchanged water. One gram of horny layer was suspended in 20–50 ml of 50 mM Tris-HCl buffer solution (pH 8.0) containing 25 mM β-mercaptoethanol, and the suspension was stirred overnight. The swollen horny layer was ground with a TEFLON ® homogenizer and was centrifuged (30,000×g, 30 min.) The supernatant was filtered using filter paper and the filtrate was dialyzed against ion-exchange water. The freeze-dried powder was used as keratin fiber in the test.

(2-2) Measurement of hydrolysis power

To a 0.1 M carbonate buffer solution (pH 10.5), prepared keratin fiber and protease were added to a concentration of 1 mg/ml and $2\times10^{-3}$ APU/ml, respectively. The mixture was incubated for a prescribed period of time at 30° C. while stirring with a magnetic stirrer at a rotation of 100 rpm (stirrer piece, 35 mm). After the addition of phenylmethylsulfonyl fluoride to a final concentration of 2 mM, the solution was filtered through a 0.5 μm membrane filter. Solubilizable proteins, as converted to tyrosine in the filtrate were measured by the Lowry method.

(2-3) Calculation of the hydrolyzing power for human horny keratin fiber

The amount of protease which can produce solubilizable proteins as hydrolysis products corresponding to 1 mg of tyrosine per minute from human horny keratin fiber is defined as 1 KFU.

Enzymological Characteristics of Alkaline Protease K-16

(1) Hydrolysis action

Acts on various kinds of proteins user high alkaline conditions, especially exhibits 48 KFU/APU of activity for human horny keratin fiber.

(2) Substrate specificity

The specificity toward various substrates of alkaline protease K-16 and commercial protease were compared. Substrates used were casein, urea-denatured hemoglobin, animal hair keratin, and elastin. Degradation activities of the enzymes for these substrates were measured. Each substrate was added to 50 mM borate-NaOH buffer (pH 10.0) to make its concentration 1% (2.2% for urea-denatured hemoglobin), and each enzyme was added in an amount of $0.5\times10^{-4}$ PU ($3.5\times10^{-4}$ PU for elastin). The reaction mixture was incubated at 40° C. for 10 minutes. The activity of each enzyme toward each substrate is shown in Table 3, wherein the activity of alkaline protease K-16 is taken as 100.

TABLE 3

| Enzyme | Substrate | | | |
|---|---|---|---|---|
| | Casein | Urea-denatured hemoglobin | Animal hair keratin | elastin |
| K-16 | 100 | 100 | 100 | 100 |
| Commercial enzyme A[1] | 100 | 108 | 100 | 77 |
| Commercial enzyme B[2] | 100 | 100 | 103 | 76 |

[1] SAVINASE ® (Novo Nordisk Ltd.)
[2] PROTEASE API-21 ® (Showa Denko K.K.)

As shown in the above Table, alkaline protease K-16 of the present invention exhibits excellent hydrolysis activity for both water-soluble and water-insoluble proteins. It possesses better hydrolysis activity, particularly for elastin, than Commercial Enzymes A and B which are widely used as enzymes for detergents due to their hydrolysis activity.

(3) Optimum pH range

Figure 1:
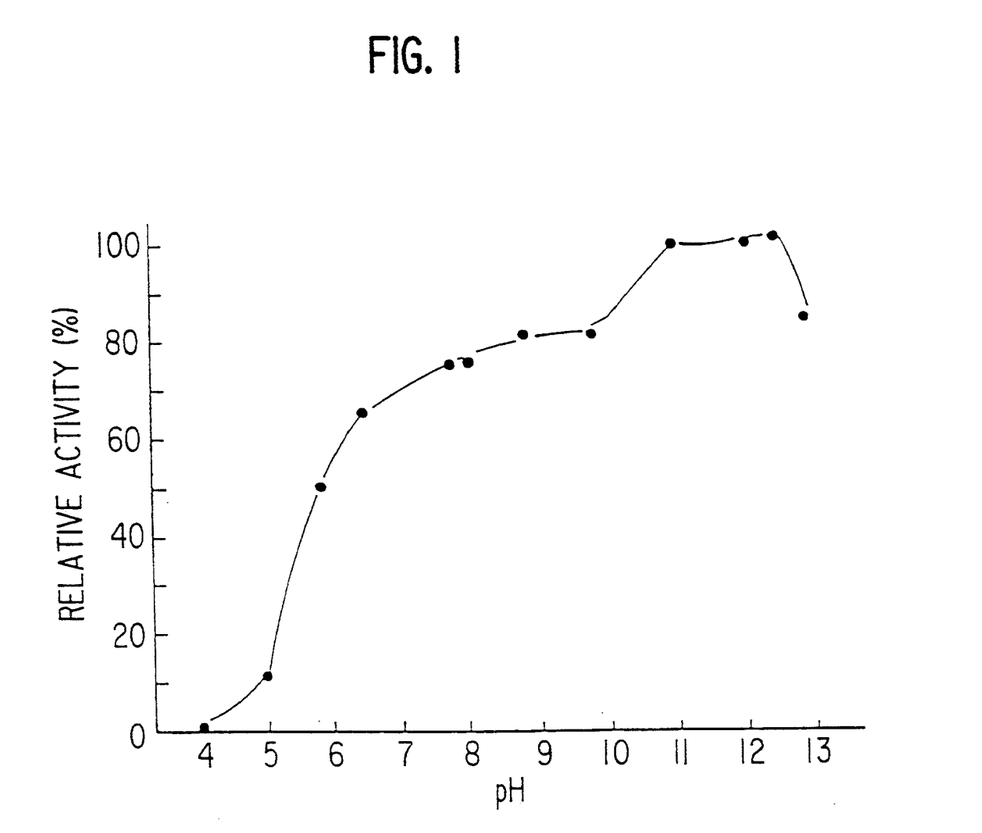
FIG. 1 illustrates the influence of pH on the activity of alkaline protease K-16.

Casein was added to various buffer solutions (50 mM) to a final concentration of 0.91%, and then $5.2\times10^{-5}$ PU of alkaline protease K-16 was added to the solution. The mixture was incubated at 40° C. for 10 minutes to measure the enzymatic activity. Activities of the enzyme at various pH values relative to optimum pH (100%) are shown in FIG. 1, which indicates that the optimum pH range of alkaline protease K-16 of the present invention is 11.0–12.3. The buffer solutions used in the measurement and their pH values are as follows.

Acetate buffer: pH 3.9–5.7

Phosphate buffer: pH 6.6–8.3
Carbonate buffer: pH 9.2–10.9
Phosphate-NaOH buffer: pH 10.9–12.7
KCl-NaOH buffer: pH 10.9–12.6

Figure 2:
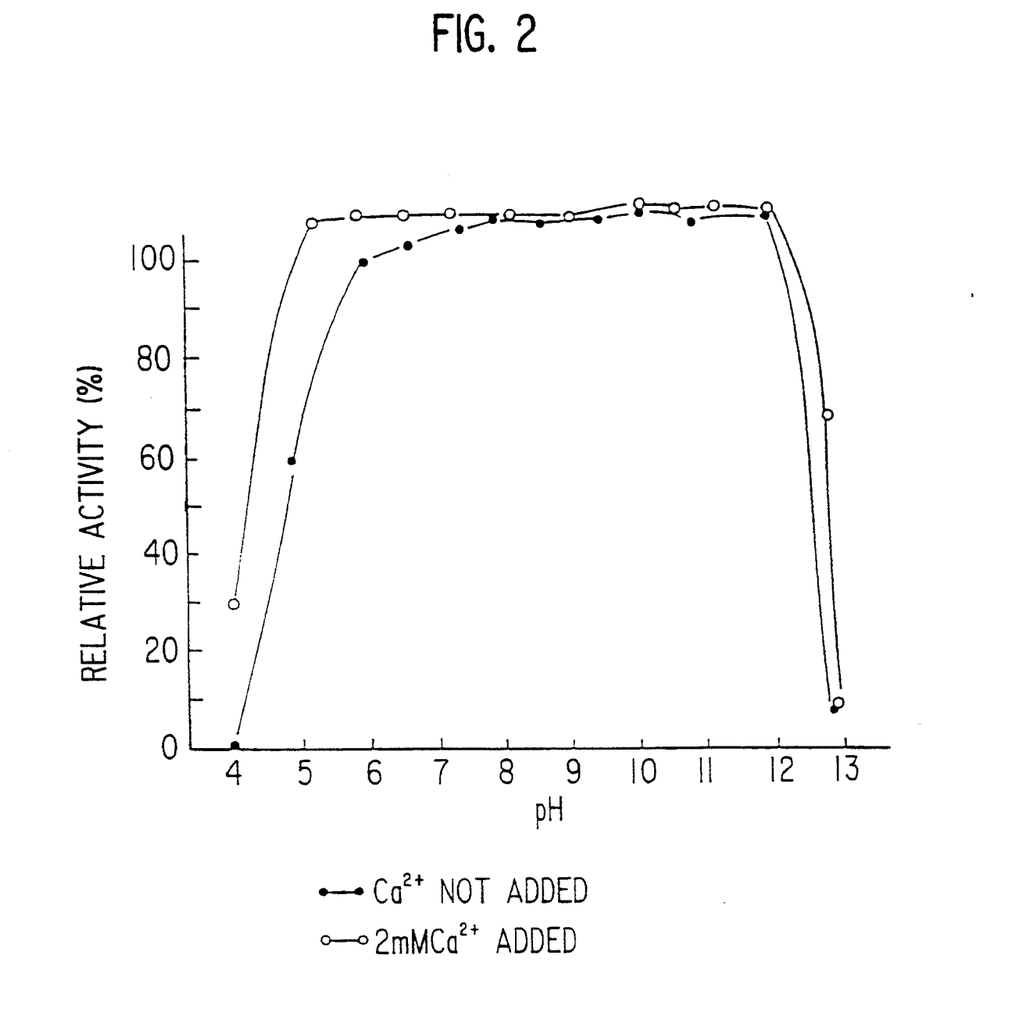
FIG. 2 illustrates the influence of pH on the stability of alkaline protease K-16.

(4) pH stability $7.9\times10^{-3}$ PU of alkaline protease K-16 was added to the same buffer solutions (20 mM) as used in (3) above. The solution was allowed to stand at 25° C. for 48 hours and diluted with 50 mM borate-NaOH buffer (pH 10.0) to a volume of 40 folds to measure the enzymatic activity. Activities of the enzyme relative to the activity before the treatment (100%) were determined, and the results are shown in FIG. 2, which shows the stable pH range of alkaline protease K-16 is 6.0–12.0 in the absence of $Ca^{2+}$ and 5.0–12.0 in the presence of 2 mM $Ca^{2+}$.

Figure 3:
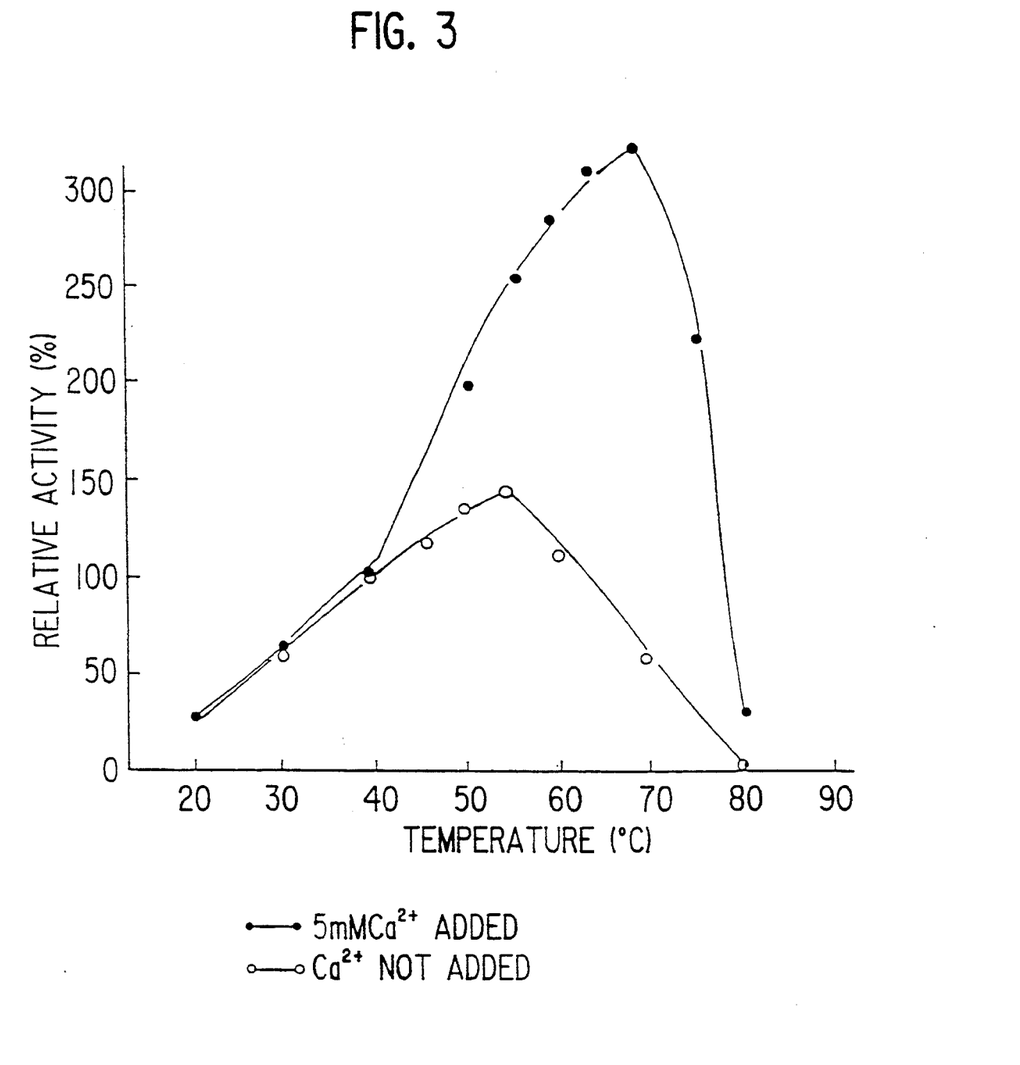
FIG. 3 illustrates the influence of temperature on the activity of alkaline protease K-16.

(5) Optimum temperature $3.1\times10^{-5}$ PU of alkaline protease K-16 was added to 50 mM borate-NaOH buffer (pH 10.0) which contained 0.91% of casein and incubated at various temperatures for 10 minutes. Activities of the enzyme at each temperature relative to the activity at 40° C. (100%) were determined and the results are shown in FIG. 3, which shows the optimum temperature range of alkaline protease K-16 is 55° C. in the absence of $Ca^{2+}$ and 70° C. in the presence of 5 mM $Ca^{2+}$.

Figure 4:
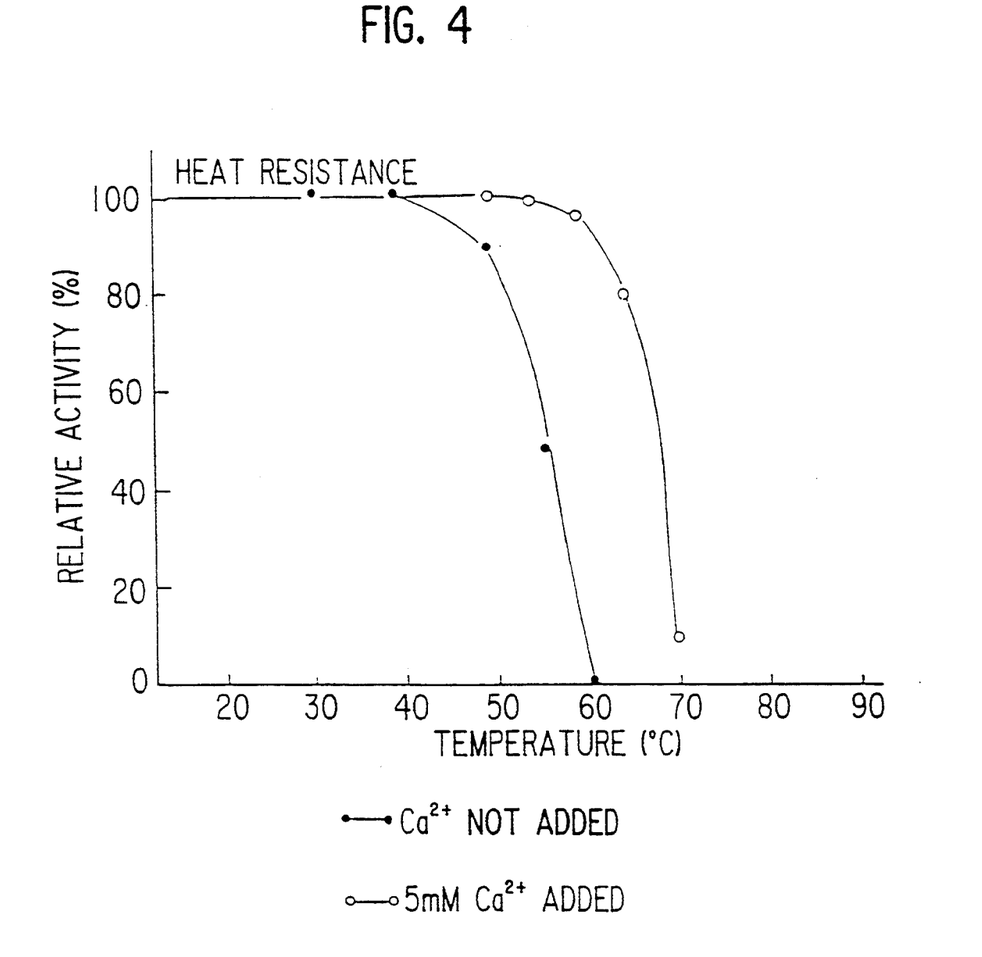
FIG. 4 illustrates the influence of temperature on the stability of alkaline protease K-16.

(6) Heat stability $1.6\times10^{-3}$ pU of alkaline protease K-16 was added to 20 mM borate-NaOH buffer (pH 9.5) and heated at various temperatures for 10 minutes. After cooling, the solution was diluted to a volume of 5 folds with 50 mM borate-NaOH buffer
(pH 10.0), and the enzymatic activity was measured using 0.91% casein as a substrate. Activities of the enzyme at each temperature relative to the activity before the treatment (100 ) were determined and the results are shown in FIG. 4, which shows alkaline protease K-16 maintained 90% or more of the activity up to 50° C. in the absence of $Ca^{2+}$ and up to 60° C. in the presence of 5 mM $Ca^{2+}$ (7) Molecular weight The molecular weight of alkaline protease K-16 was measured by sodium dodecyl sulfonate (SDS)-polyacrylamide gel electrophoresis. As molecular weight (M.W.) markers, a low M.W. marker kit (Bio-Rad); phosphorilase b (M.W. 97,400), FCS albumin (M.W. 66,200), ovalbumin (M.W. 42,700), carbonic anhydrase (M.W. 31,000), soybean trypsin inhibitor (M.W. 21.500), lysozyme (M.W. 14,400); was used. The molecular weight of alkaline protease K-16 of the present invention was found to be 28,000±1000 by the measurement by this method.

(8) Isoelectric point

The isoelectric point of alkaline protease K-16 was examined by the electrofocusing method using Servalyte 9-11 as an amphoteric carrier for the column. The isoelectric point of alkaline protease K-16 of the present invention was determined by this method as over 10.5.

(9) Effects of metal ions

The effects of various metal ions on alkaline protease K-16 were examined. Various metal ions were added to 20 mM borate-NaOH buffer solution (pH 9.5) to a concentration of 1 mM. $3.9\times10^{-3}$ PU of alkaline protease K-16 was added to the buffer solutions and allowed to stand at 30° C. for 20 minutes. The resulting solution was diluted with 50 mM borate-NaOH buffer solution (pH 10.0) to a volume of 5 folds to measure the residual enzyme activity. Residual activities were expressed as the relative activity to the enzyme activity without the addition of a metal ion. The results are shown in Table 4, which shows the activity of alkaline protease K-16 of the present invention is inhibited by $Hg^{2+}$ and $Cu^{2+}$.

Also, from the results of (5) and (6) above $Ca^{2+}$ promotes the heat stability of the enzyme.

TABLE 4

| Metal salt (1 mM) | Residual Activity (%) |
|---|---|
| Not added | 100 |
| $ZnCl_2$ | 106 |
| $AgNO_3$ | 86 |
| $CaCl_2$ | 103 |
| $NiCl_2$ | 103 |
| $CoCl_2$ | 103 |
| $PbCl_2$ | 100 |
| $HgCl_2$ | 46 |
| $CuSO_4$ | 73 |

(10) Effects of inhibitors

Effects of enzyme inhibitors generally used on alkaline protease K-16 were examined. The tested inhibitors were added to 10 mM phosphate buffer (pH 7.0) to a prescribed concentration. $7.9 \times 10^{-3}$ PU of alkaline protease K-16 was then added to the buffer solutions and allowed to stand at 30° C. for 20 minutes. The resulting solution was diluted with deionized water to a volume of 20 folds to measure the residual enzyme activity. Residual activities were expressed as the relative activity to the enzyme activity without the addition of an inhibitor. The results are shown in Table 5, which shows the activity of alkaline protease K-16 of the present invention is inhibited by diisopropyl fluorophosphate (DFP), phenylmethanesulfonyl fluoride (PMSF), and chymostatin which are serine protease inhibitors, demonstrating that it is an enzyme with a serine residue at its active center.

TABLE 5

| Inhibitor | Concentration | Residual activity (%) |
|---|---|---|
| Not added | — | 100 |
| EDTA | 5 mM | 107 |
| PCMB | 1 mM | 100 |
| DFP | 1 mM | 3.8 |
| PMSF | M | 1.5 |
| Antipine | 0.01% | 108 |
| Chymostatin | 0.01% | 34 |

EDTA: Ethylenediaminetetraacetic acid
CMB: 4-Chrolomercuribenzoate
DFP: Diisopropyl fluorophosphatic acid
PMSF: Phenylmethanesulfonyl fluoride (11) Effects of surface active agents Various surface active agents were dissolved in 0.1 M Tris HCl buffer (pH 9.0; contains 10% of ethanol), and $6.6 \times 10^{-2}$ P.U. of alkaline protease K-16 was added to the solution. The mixture was allowed to stand at 40° C. for 4 hours. The resulting solution was diluted with 50 mM borate-NaOH buffer solution (pH 10.0) to a volume of 20 folds to measure the residual enzyme activity. Residual activities were expressed as percentages of the original activity (no treatment), taken as 100%.

The results are shown in Table 5, which shows that the activity of alkaline protease K-16 of the present invention remains stable in the presence of various surface active agents at high concentrations (1–10%).

Thus, the alkaline protease K-16 is useful as a component of a detergent composition which contains surface active agents.

TABLE 6

| Surfantant (Concentration) | K-16 | Commercial Enzyme B[a] | Commercial Enzyme C[b] |
|---|---|---|---|
| Sodium linear alkylbenzene sulfonate *1 (1%) | 65(%) | 48(%) | 46(%) |
| Sodium polyoxyethylene alkyl sulfate *2 (1%) | 100 | 97 | 52 |
| Sodium dodecyl sulfate *3 (10%) | 58 | 0 | 48 |
| Sodium α-olefin sulfonate *4 (1%) | 100 | 82 | 61 |
| Sodium alkyl sulfonate *5 (10%) | 81 | 23 | 72 |
| α-Sulfo-fatty acid ester *6 (1%) | 100 | 86 | 75 |
| Softanol 7OH *7 (1%) (a product of Nippon Shokubai Co.) | 100 | 84 | 90 |

[a] PROTEASE API-21 ® (Showa Denko K.K.)
[b] ESPERASE ® (Novo Nordisk Ltd.)

*1 R—⟨O⟩—$SO_3Na$ (R: $C_{10}$–$C_{14}$)

*2 R—$CH_2O(C_2H_4O)_nSO_3Na$(R: $C_9$–$C_{17}$, n = 1–5)
*3 R—$CH_2OSO_3Na$(R: $C_9$–$C_{17}$, But the $C_{12}$ is principal)
*4 R—CH=$CH(CH_2)_nSO_3Na$(R: $C_7$–$C_{15}$, n = 0.1–5)
*5 R—CH—R' (R + R': $C_{13}$–$C_{18}$)
    |
    $SO_3Na$
*6 R—CH—COCR' (R: $C_{10}$–$C_{16}$, R': $C_1$–$C_6$)
    |
    $SO_3Na$
*7 R—$CH_2O(C_2H_4O)_nH$(R: $C_8$–$C_{17}$, n = 5–15)

Enzymological Characteristics of Alkaline Protease 14

(1) Hydrolysis action

Acts on various kinds of proteins under high alkaline conditions, especially exhibits 50 KFU/APU of activity for-human horny keratin fiber.

(2) Optimum pH range

Figure 5:
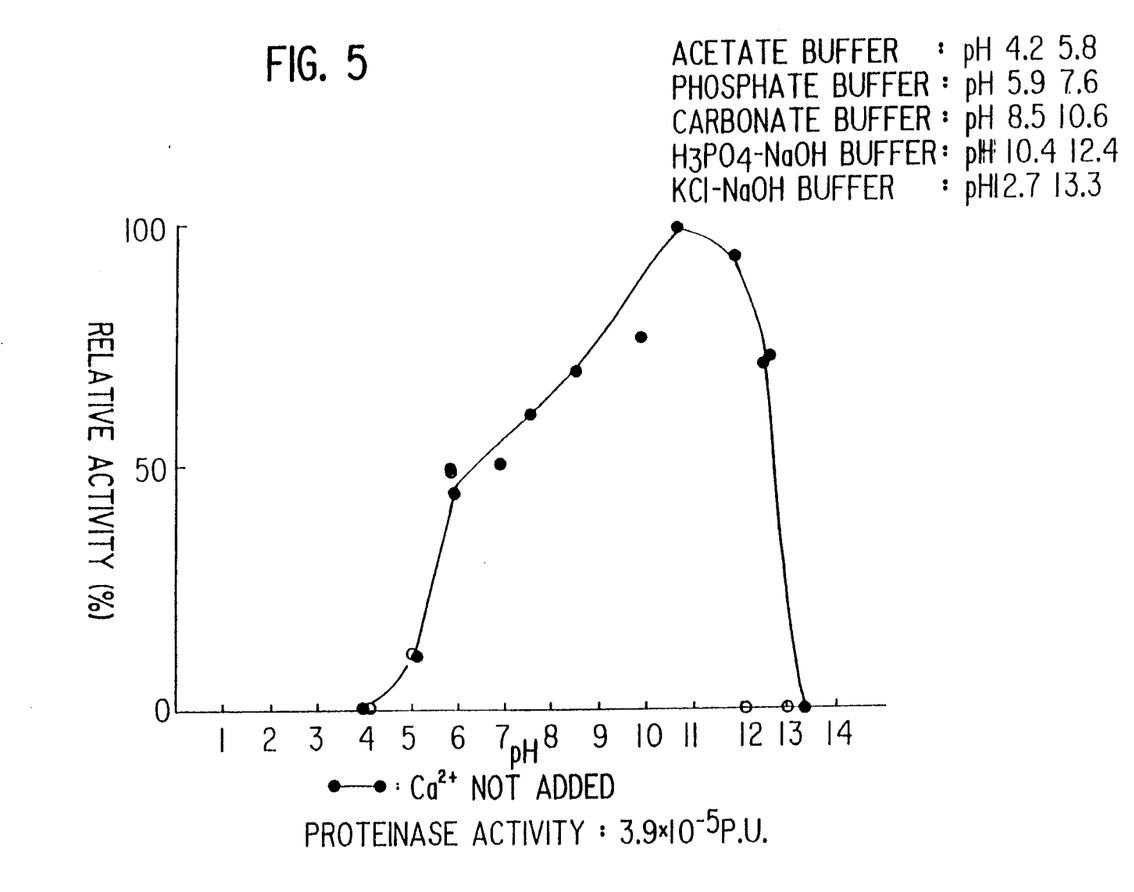
FIG. 5 illustrates the influence of pH on the activity of alkaline protease K-14.

The optimum pH range of alkaline protease K-14 was determined in the same manner as for alkaline protease K-16. As shown in FIG. 5, the range was found to be 10.4–12.0.

(3) pH stability

Figure 6:
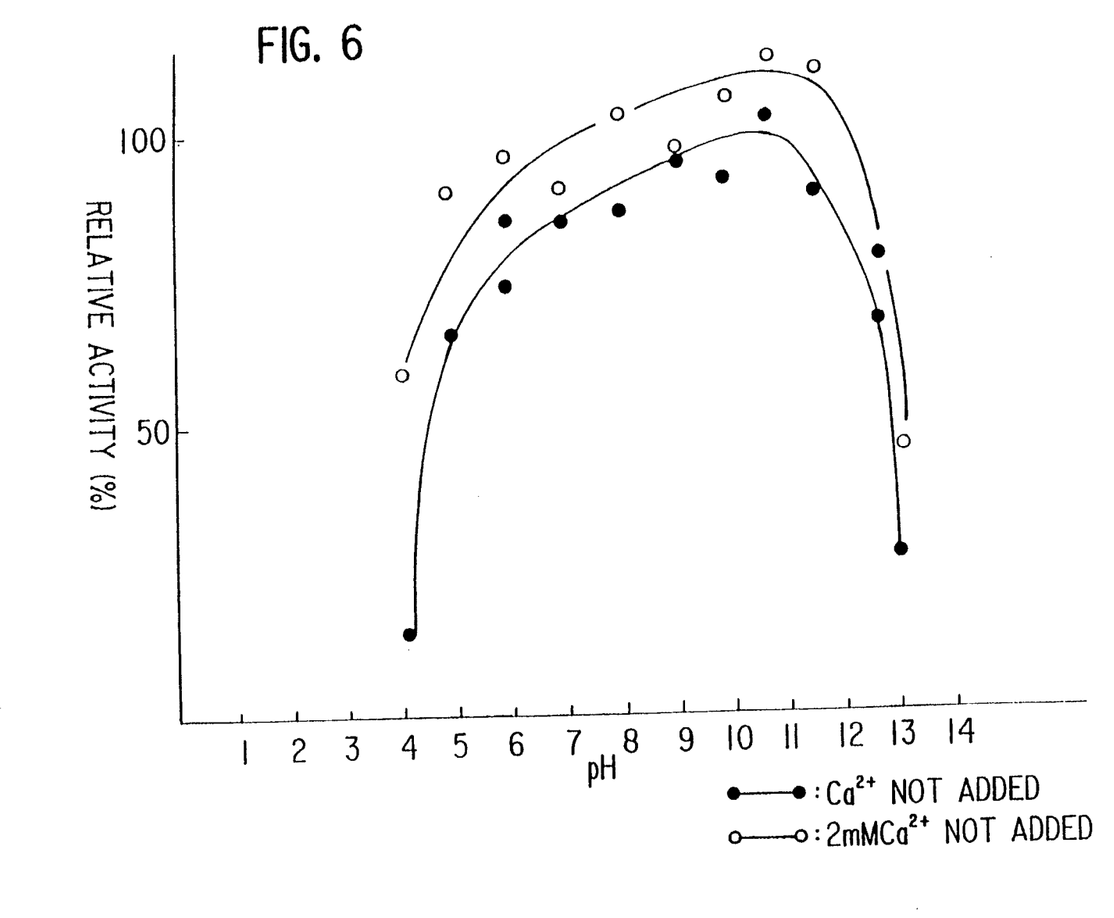
FIG. 6 illustrates the influence of pH on the stability of alkaline protease K-14.

The pH stability of alkaline protease K-14 was determined in the same manner as for alkaline protease K-16. As shown in FIG. 6, the stable pH range of alkaline protease K-14 is 7–11.5 in the absence of $Ca^{2+}$ and 5–12 the presence of 2mM $Ca^{2+}$.

(4) Optimum temperature

Figure 7:
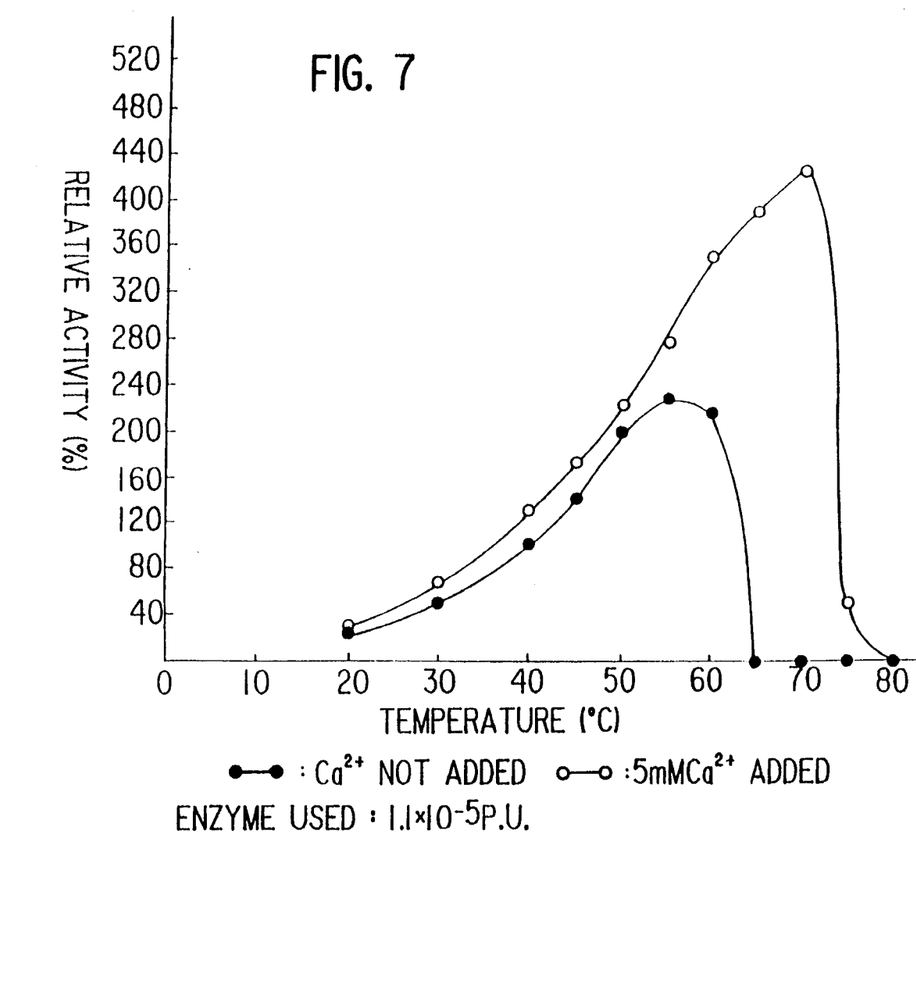
FIG. 7 illustrates the influence of temperature on the activity of alkaline protease. K-14.

The optimum temperature of alkaline protease K-14 was determined in the same manner as for alkaline protease K-16. As shown in FIG. 7, the optimum temperature of alkaline protease K-14 is 55° C. in the absence of $Ca^{2-}$ and 70° C. in the presence of 5 mM $Ca^{2+}$.

(5) Heat stability

Figure 8:
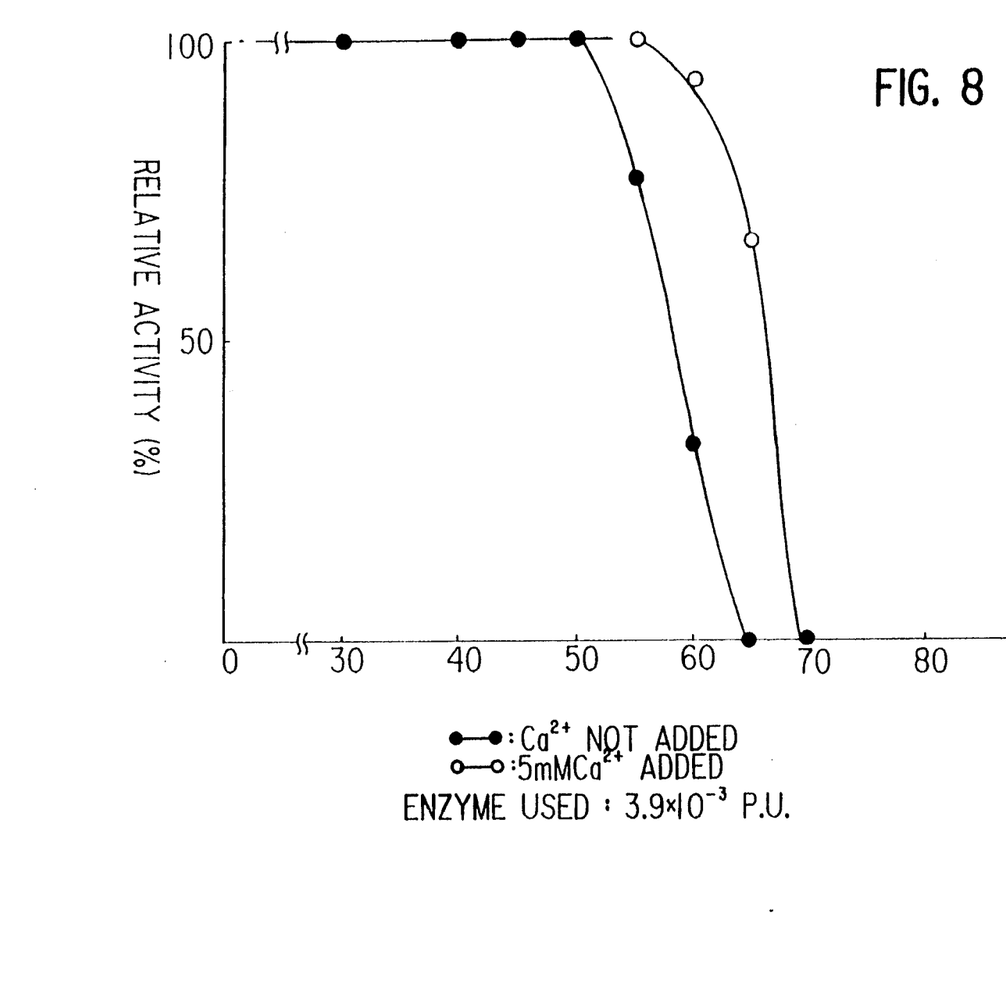
FIG. 8 illustrates the influence of temperature on the stability of alkaline protease K-14.

The heat stability of alkaline protease K-14 was studied in the same manner as for alkaline protease K-16. As shown in FIG. 8, alkaline protease K-14 maintained 90% or more of the activity up to 50° C. in the absence of $Ca^{2+}$ and up to 60° C. in the presence of 5 mM $Ca^{2+}$.

(6) Isoelectric point

The isoelectric point of alkaline protease K-14 was examined by using Rhotophore electrophoresis kit (Trademark, made by Bio-Rad Co.). As a result, the isoelectric point of alkaline protease K-14 was found to be over 10.0.

Detergent Compositions

There are no specific limitations as to the amount of the above alkaline protease to be incorporated into the detergent compositions of the present invention, so long as the amount of the incorporation permits the enzymes to exhibit their activity. A preferable range is 0.1–6,000 APU per 1 kg of the detergent composition, with a particularly preferable range being 5–400 APU.

Any known detergent components can be formulated in the detergent compositions of the present invention. The following compounds are given as examples of such known detergent components.

(1) Surface active agents

Anionic surface active agents such as linear alkylbenzene sulfonates having an alkyl group containing 10 to 16 carbon atoms on average, alkylethoxy sulfates having a linear or branched alkyl group containing 10 to 20 carbon atoms on average and 0.5–8 moles on average of ethylene oxide per molecule, alkyl sulfates having an alkyl group containing 10 to 20 carbon atoms on average, olefin sulfonates containing 10 to 20 carbon atoms on average per molecule, alkane sulfonates containing 10 to 20 carbon atoms on average per molecule, salts of $\alpha$-sulfo-fatty acid methyl or ethyl esters containing 10 to 20 carbon atoms on average per molecule, salts of higher fatty acids containing 8 to 20 carbon atoms on average, alkylether carboxylates having a linear or branched alkyl group containing 10 to 20 carbon atoms on average and 0.5–8 moles on average of ethylene oxide per molecule, and the like; nonionic surface active agents such as polyoxyethylene alkyl ethers having an alkyl group containing 10 to 20 carbon atoms on average and 1–20 moles on average of ethylene oxide per molecule, higher fatty acid alkanolamides or their alkylene oxide adducts, and the like; betaine-type amphoteric surface active agents; sulfonate-type amphoteric surface active agents; phosphate-type surface active agents; amino acid-type surface active agents; cationic surface active agents; and the like.

These surface active agents can be incorporated into the detergent composition of the present invention in an amount of 5–60% by weight; especially 10–45% by weight in powder detergent compositions and 20–55% by weight in liquid detergent compositions. When the detergent composition is directed to bleaching, the amount of surface active agents may be 1–10% by weight, and preferably 1–5% by weight.

(2) Divalent metal ion capturing agents

Condensed phosphates such as tripolyphosphate, pyrophosphate, orthophosphate, and the like; aluminosilicates such as zeolites; synthetic layer crystalline silicate, nitrilotriacetate, ethylenediaminetetraacetic acid, citric acid, isocitric acid, polyacetal carboxylate, and the like.

Such divalent metal ion capturing agents can be incorporated into the detergent composition of the present invention in an amount of 0–50% by weight, and preferably 5–40% by weight in powder detergent composition and 0.5–15% by weight in liquid detergent composition. Use of divalent metal ion capturing agents not containing phosphorous is preferable.

(3) Alkaline agents and inorganic salts

Silicates, carbonates, sesquicarbonates, alkanolamine sulfates, and the like. These are added in an amount of 0–80% by weight, preferably 5 to 50% by weight in powder detergent composition, and 0.1 to 25% by weight in liquid detergent composition.

(4) Secondary pollution inhibitors

Polyethylene glycol, polyacrylates, polyacrylic acid copolymers, polyvinyl alcohol, polyvinylpyrrolidone, carboxymethyl cellulose, and the like. These pollution inhibitors are added in an amount of 0–10% by weight, and preferably 1–5% by weight.

(5) Enzymes

Cellulase, amylase, lipase, hemicellulase, $\beta$-glycosidase, glucose oxidase, cholesterol oxidase, alkaline proteases other than alkaline proteases of the present invention. The above alkaline proteases of the present invention exhibit better compatibility with other enzymes such as cellulase and lipase than conventionally known alkaline proteases. Combined use of the alkaline proteases of the present invention with these other enzymes promotes the detergency even more.

(6) Capturing or reducing agents of effective chlorine in city water

Given as examples of capturing agents of effective chlorine are ammonium sulfate, urea, guanidine hydrochloride, guanidine carbonate, guanidine sulfamate, dioxythiourea, monoethanolamine, diethanolamine, triethanolamine, amino acids, e.g., glycine, sodium glutamate, etc.; proteins, e.g., calf serum albumin casein, etc.; protein hydrolyzates, meat extract, fish extract, and the like.

As reducing agents, salts of an alkali metal or alkaline earth metal, such as thiosulfates, sulfites, or dithionites, as well as RONGALIT C ®, can be used. Such agents are suitably added in an amount of 0 to 5% by weight, preferably 0.1 to 2% by weight.

(7) Bleaching agents

Percarbonates, perborates, zinc or aluminum sulfonated phthalocyanine, hydrogen peroxide, and the like can be used, in amounts ranging from 0 to 50% by weight.

(8) Fluorescent dyes

Fluorescent dyes commonly used in detergent compositions can be used, in amounts of 0 to 5% by weight, preferably 0.1 to 2% by weight.

(9) Solubilizing agents

The following solubilizing agents can be used for liquid detergent compositions.

Lower alcohols, e.g., ethanol; lower alkyl benzene sulfonates, e.g., benzene sulfonates, p-toluene sulfonates; polyols, e.g., propylene glycol; and the like can be added in amounts ranging from 0 to 25% by weight to 0.5 to 18% by weight.

(10) Other components

Besides the above components, perfumes, caking preventives, enzyme activators, antioxidants, antiseptics, pigments, greenish flavoring agents, bleaching activators, and the like which are commonly used in detergent compositions can be formulated in the detergent compositions of the present invention as required.

The detergent compositions of the present invention can be prepared by conventional methods by combining the above-mentioned alkaline proteinases and other known detergent components. The form of the detergent composition may be liquid, powder, granule, or the like depending on the application, which includes detergents for washing clothes, automatic dish washing machines, water pipes, false teeth, or the like, as well as bleaching agents.

The detergent compositions of the present invention comprise an alkaline protease e.g., alkaline protease K-16 or K-14 produced by Bacillus sp. KSM-K16 (FERM BP-3376) or Bacillus sp. KSM-K14 (FERM BP-3670), which is highly active under alkaline conditions, resistant to alkali and capable of hydrolyzing human horny keratin fiber. It exhibits superior detergency against protein soils.

Other features of the invention will become apparent in the course of the following description of the exemplary embodiments which are given for illustration of the invention and are not intended to be limiting thereof.

EXAMPLES

Reference Example 1.

Separation and collection of proteinase-producing microorganism (1) About 1 g of a soil sample was suspended in 10 ml of sterilized physiological saline and heat-treated at 80° C. for 20 minutes. A supernatant of the heat-treated suspension (0.1 ml) was spread on a keratin agar medium and cultivated at 30° C. for 48 hours. The composition of the keratin agar medium was as follows.

Glucose: 1%
Yeast extract: 0.2%
Animal hair keratin: 1%
Carboxymethyl cellulose: 1%
Potassium (I) phosphate: 0.1%
MgSO$_4$.7H$_2$O: 0 02%
Agar: 1.5%

(2) To the above keratin agar medium was added 1% of sterilized 10% sodium carbonate solution to adjust the pH 10.5. After the cultivation, colonies that formed a clear zone around their margins were picked up and repeatedly purified on the same agar medium, thus obtaining a pure proteinase producing microorganisms.

(3) Cells obtained in (2) above were inoculated into the liquid medium with the following composition and cultured at 30° C. for 2 days, with shaking, on a reciprocal shaker.

Glucose: 2.0%
Polypepton S: 1.0%
Yeast extract: 0.05%
Potassium (I) phosphate: 0.1%
MgSO$_4$.7H$_2$O: 0.02%
Sodium carbonate (separately sterilized): 1.0%
pH: 10.5

After the cultivation, the culture broth was centrifuged (3,000 rpm, 10 minutes) to remove cells to obtain a supernatant as an enzyme solution.

(4) Crude enzyme samples were prepared by lyophilizing the enzyme solutions obtained in (3) above. The storage stability of the enzymes at 40° C. in a commercial detergent was evaluated. A strain which can produce enzymes in a most stable manner were thus obtained as Bacillus sp. KSM-K16 and Bacillus sp. KSM-K14.

REFERENCE EXAMPLE 2

Cultivation of Cells and Purification of Alkaline Proteinase K-16

(1) The alkalophilic Bacillus sp. KSM-K16 obtained in Reference Example 1 was inoculated into the following liquid medium (3.0 l) and cultured at 30° C. for 2 days, with shaking, to produce alkaline protease K-16.

Glucose: 2.0%
Fish meat extract: 1.0%
Soybean flour: 1.0%
MgSO$_4$.7H$_2$O: 0.02%
Potassium (I) phosphate: 0.1%
pH: 10.5

(2) After the cultivation, 3.0 l of the culture broth was centrifuged (10,000 rpm, 5 minutes) to remove cells. The supernatant thus obtained was lyophilized and 2 g of the dried powder was dissolved in 10 ml of deionized water to produce a crude enzyme solution. The solution was dialyzed overnight against 10 mM Tris-HCl buffer (contains 2 mM Ca$^{2+}$, pH 7.5) and 26 ml of retentate (activity, 3.15 P.U./ml; specific activity, 1.97 P.U./mg protein) was obtained. This retentate was subjected to a column packed with CM-52 cellulose which had been equilibrated with 10 mM Tris-HCl buffer (contains 2 mM Ca$^{2+}$, pH 7.5). After washing the column with the equilibrating buffer, alkaline protease K-16 was eluted with a gradient of 0 to 0.15 M sodium chloride in the same buffer. The active fractions collected was 15 ml, and its activity was found to be 1.12 P.U./ml and the specific activity 5.75 P.U./mg protein. The active fraction was dialyzed overnight against 50 mM Tris-HCl buffer (contains 10 mM Ca$^{2+}$ and 0.2 M NaCl, pH 8.0), concentrated by ultrafiltration (5000-M.W. out off; Amicon Co.), applied to a column of Sephadex G-50 (Pharmacia) which had been equilibrated with 50 mM Tris-HCl buffer (contains 10 mM Ca$^{2+}$ and 0.2 M NaCl, pH 8.0), and elution was done with the same buffer. The active fractions collected was 11.5 ml, and its activity was 0.9 P.U./ml and the specific activity was 6.03 P.U./mg protein.

The solution was dialyzed overnight against deionized water to obtain a retentate with an activity of 0.56 P.U./ml and a specific activity of 5.60 P.U./mg protein.

This solution was lyophilized to obtain an enzyme with a specific activity of 1.87 APU/mg and an activity of hydrolyzing human horny keratin fiber of 48 KFU/APU.

REFERENCE EXAMPLE 3

Cultivation of Cells and Purification of Alkaline Proteinase K-14.

(1) The alkalophilic strain Bacillus sp. KSM-K14 obtained in Reference Example 1 was inoculated into the following liquid medium (3.0 l) and cultured at 30° C. for 2 days with shaking to produce alkaline protease K-14.

Glucose: 2.0%
Fish meat extract: 1.0%
Soybean flour: 1.0%
MgSO$_4$.7H$_2$O: 0.02%
Potassium (I) phosphate: 0.1%
pH: 10.0

(2) A powder of pure alkaline proteinase K-14 was prepared by the cultivation of the microorganism and the purification of the culture broth in the same manner as in Reference Example 2. The activity of hydrolyzing human horny keratin fiber of the enzyme was 50 KFU/APU.

Detergent Tests

The detergent tests in the Examples hereinafter given were conducted according to the following procedures.

(1) Naturally soiled collar

Pieces of cotton cloth (#2023; 9 cm × 30 cm) were sewn on the collars of shirts, and the shirts were worn by male adults for 3 days, following which they are left at 25° C., 65% RH (relative humidity) for 1 month. The clothes were classified into 3 groups according to the degree of soil. Among the most soiled clothes, those having symmetric soil across the center were cut along the center line into 2 pieces to prepare specimens (9 cm×15cm) to be used in the test.

(2) Washing method and conditions

One half of the 2 pieces of cloth specimens prepared as above was washed with a standard detergent composition to which no enzyme was added, and the other with the detergent composition of the present invention. 15 pieces of specimens were sewn onto a 50 cm×50 cm cloth. In the test of powder detergent compositions, this cloth and undershirts, weighing 1 kg in total, were dipped into 6 l of a 0.417% detergent solution at 30° C. for 2 hours. The content was transferred to a washing machine (Ginga: trademark, manufactured by Toshiba Co.). After making the total volume 30 l with addition of water, the content was vigorously stirred for 10 minutes. The clothes were dried and used for the evaluation.

For the evaluation of liquid detergent compositions, 20 cc of the detergent liquid was applied to samples of cloth to be tested. After 10 minutes, the cloth together with undershirts, weighing 1 kg in total, were transferred to a washing machine (Ginga). After making the total volume 30 l with addition of water, the content was vigorously stirred for 10 minutes. The clothes were dried and served for the evaluation.

The evaluation was carried out by visual judgment, whereby the clothes washed with the standard detergent composition and the clothes washed with the detergent composition of the present invention were compared with the standard soil samples which were ranked into 10 grades according to the degree of soil. The detergency index was expressed by the scores of each composition when the detergency of the standard detergent composition was taken as 100. A difference in the detergency index of more than 0.5 was deemed meaningful.

(3) Enzymes used in Examples (a) Alkaline protease K-16 (the product obtained in Reference Example 2 diluted to a volume of 200-fold with Glauber's salt and made into granules).

(b) Alkaline protease K-14 (the product obtained in Reference Example 2 diluted to a volume of 200-fold with Glauber's salt and made into granules).

(c) Protease (a product of Novo Nordisk Co.; SAVINASE 4.0T ®)

(d) Protease (a product of Gist Brocades Co.; MAXACAL P-400,000 ®)

(e) Protease (a product of Showa Denko Co., Ltd.; API-21H ®)

(f) Cellulase (Kao Corp., derived from microorganism thrombomodulin FIRM 1138, 500 IU/g granules)

(g) Cellulase (a product of Novo Nordisk -Co.; CELLUZYME 1.0T ®)

(h) Lipase (a product of Novo Nordisk Co.; LIPOLASE 100T ®)

Example 1

Weakly alkaline powder detergent compositions were prepared according to the formulation shown in Table 7 and using the enzymes listed in Table 8.

The results of the evaluation of the detergent compositions are given in Table 8, which shows superior detergency of the detergent composition of the present invention in removing naturally produced soil on collars.

TABLE 7

| Components | wt % |
|---|---|
| Sodium linear alkylbenzene sulfonate (LAS) ($C_{12}$) | 25 |
| Sodium alkyl sulfate (AS) ($C_{14}$) | 10 |
| Polyoxyethylene alkyl ether (AE) ($C_{12}$-$C_{13}$, EO = 12 moles) | 2.5 |
| Sodium hydrogenated tallow | 2.5 |
| Polyethylene glycol (Average M.W. = 12,000) | 1.5 |
| Sodium polyacrylate (Average M.W. = 8,000) | 1.5 |
| 4A-type Zeolite | 25 |
| Sodium silicate (JIS #2) | 10 |
| Sodium carbonate | 10 |
| Sodium sulfite (anhydrous) | 1 |
| Fluorescent dye | 0.2 |
| Glauber's salt | Balance |
| Water | 6 |
| Enzyme (see Table 8) | Prescribed Amounts * or 0 |
| Total | 100 |

*50 APU/kg for Compositions 1-(a) to 1-(e); and 1% for Compositions 1-(f) to 1-(h);

In tables hereafter, the composition numbers are indicated by "Example No. - Enzyme No.". The compositions which do not contain any enzyme are indicated by "Example No. —0".

TABLE 8

| Composition No. | Enzyme | Detergency Index |
|---|---|---|
| 1-0 (Standard Composition) | — | 100 |
| 1-(a) (Invention Composition) | (a) | 104 |
| 1-(b) (Invention Composition) | (b) | 104. |
| 1-(c) (Comparative Composition) | (c) | 101 |
| 1-(d) (Comparative Composition) | (d) | 101 |
| 1-(e) (Comparative Composition) | (e) | 102 |
| 1-(f) (Comparative Composition) | (f) | 101.5 |
| 1-(g) (Comparative Composition) | (g) | 101 |
| 1-(h) (Comparative Composition) | (h) | 100.5 |

Example 2

Weakly alkaline powder detergent compositions as shown in Table 7 with various combinations of the enzymes [(a) to (h)] as shown in Table 9 were prepared. The results of the detergency test are given in Table 9, which demonstrates a synergistic effect, in detergency toward naturally produced soil in collars of the combined use of alkaline protease K-16 and cellulase and/or lipase.

TABLE 9

| Composition No. | Enzyme Combination (dosage per kg - detergent) | Detergent Index |
|---|---|---|
| 2-(a) (Invention Composition) | (a) = 50 APU | 100 |
| 2-(e) (Comparative Composition) | (e) = 50 APU | 98 |
| 2-(f) (Comparative Composition) | (f) = 1% | 97.5 |
| 2-(g) (Comparative Composition) | (g) = 1% | 97 |
| 2-(h) (Comparative Composition) | (h) = 1% | 96.5 |
| 2-(a)/(f) (Invention Composition) | (a)/(f) = 25 APU/0.5% | 105 |

TABLE 9-continued

| Composition No. | Enzyme Combination (dosage per kg - detergent) | Detergent Index |
| --- | --- | --- |
| 2-(a)/(g) (Invention Composition) | (a)/(g) = 25 APU/0.5% | 104 |
| 2-(a)/(h) (Invention Composition) | (a)/(h) = 25 APU/0.5 | 102 |
| 2-(a)/(f)/(h) (Invention Composition) | (a)/(f)/(h) = 25 APU/0.25%/0.25% | 106 |
| 2-(a)/(f)/(h) (Invention Composition) | (a)/(g)/(h) = 25 APU/0.25%/0.25% | 105 |
| 2-(e)/(f) (Comparative Composition) | (e)/(f) = 25 APU/0.5% | 100 |
| 2-(e)/(g) (Comparative Composition) | (e)/(g) = 25 APU/0.5 | 99 |
| 2-(e)/(f)/(h) (Comparative Composition) | (e)/(f)/(h) = 25 APU/0.25%/0.25% | 100.5 |
| 2-(e)/(f)/(h) (Comparative Composition) | (e)/(g)/(h) = 25 APU/0.25%/0.25% | 99.5 |

Example 3

Weakly alkaline powder detergent composition of the formulation shown in Table 10 were prepared, and the builders and enzymes listed in Table 11 were incorporated into the compositions in an amount indicated in Table 11. The results of the detergency test are given in Table 11, which demonstrates the effectiveness of the detergent compositions of the present invention in which various builders re incorporated.

TABLE 10

| Components | wt % |
| --- | --- |
| Sodium linear alkylbenzene sulfonate (LAS) ($C_{12}$) | 25 |
| Sodium alkyl sulfate (AS) ($C_{14}$) | 10 |
| Polyoxyethylene alkyl ether ($C_{12}$-$C_{13}$, EO-12 moles) | 2.5 |
| Sodium hydrogenated tallow | 2.5 |
| Polyethylene glycol (Average M.W. = 12,000) | 1.5 |
| Sodium polyacrylate (Average M.W. = 8,000) | 1.5 |
| Sodium silicate (JIS #2) | 10 |
| Sodium carbonate | 10 |
| Sodium sulfite (anhydrous) | 1 |
| Fluorescent dye | 0.2 |
| Glauber's salt | Balance |
| Water | 6 |
| Builders and Enzyme (see Table 11) | Prescribed Amounts * |
| Total | 100 |

*Amounts specified in Table 11.

TABLE 11

| Composition No. | Enzyme (dosage per kg) | Builder (Amount %) | | Detergency Index |
| --- | --- | --- | --- | --- |
| 3-0 (Standard Composition) | — | Tripolyphosphate | (25) | 100 |
| 3-0' (Comparative Composition) | — | Sodium citrate | (25) | 98 |
| 3-0" (Comparative Composition) | — | 4A-type Zeolite | (25) | 98.5 |
| 3-(a) (Invention Composition) | (a) = 50 APU | Tripolyphosphate | (24) | 104 |
| 3-(a)' (Invention Composition) | (a) = 50 APU | Sodium citrate | (24) | 102 |
| 3-(a)" (Invention Composition) | (a) = 50 APU | 4A-type Zeolite | (24) | 102.5 |
| 3-(b) (Invention Composition) | (b) = 50 APU | Tripolyphosphate | (24) | 104.5 |
| 3-(b)' (Invention Composition) | (b) = 50 APU | Sodium citrate | (24) | 103 |
| 3-(b)" (Invention Composition) | (b) = 50 APU | 4A-type Zeolite | (24) | 103.5 |
| 3-(e) (Comparative Composition) | (e) = 50 APU | Tripolyphosphate | (24) | 102 |
| 3-(e)' (Comparative Composition) | (e) = 50 APU | Sodium citrate | (24) | 100 |
| 3-(e)" (Comparative Composition) | (e) = 50 APU | 4A-type Zeolite | (24) | 100.5 |

TABLE 12

| Components | wt % |
| --- | --- |
| Sodium linear alkylbenzene sulfonate (LAS) | 12.5 |
| α-Sulfo-fatty acid ester (α-SFE, $C_{12}$-$C_{18}$) | 12.5 |
| Sodium alkyl sulfate (AS) | 12.5 |
| Sodium hydrogenated tallow | 2.5 |
| Polyethylene glycol (Average M.W. = 12,000) | 1.5 |
| Sodium polyacrylate (Average M.W. = 8,000) | 1.5 |
| 4A-type Zeolite | 25 |
| Sodium silicate (JIS #2) | 10 |
| Sodium carbonate | 10 |
| Sodium sulfite (anhydrous) | 1 |
| Fluorescent dye | 0.2 |
| Glauber's salt | Balance |
| Water | 6 |
| Enzyme (see Table 13) | Prescribed Amounts * or 0 |
| Total | 100 |

*50 APU/kg for Compositions 4-(a) to 4-(e); and 1% for Compositions 4-(f) to 4-(h);

TABLE 13

| Composition No. | Enzyme | Detergency Index |
| --- | --- | --- |
| 4-0 (Standard Composition) | — | 100 |
| 4-(a) (Invention Composition) | (a) | 104.5 |
| 4-(b) (Invention Composition) | (b) | 105 |
| 4-(c) (Comparative Composition) | (c) | 101.5 |
| 4-(d) (Comparative Composition) | (d) | 101 |
| 4-(e) (Comparative Composition) | (e) | 102.5 |
| 4-(f) (Comparative Composition) | (f) | 102 |
| 4-(g) (Comparative Composition) | (g) | 101.5 |
| 4-(h) (Comparative Composition) | (h) | 100.5 |

Example 4

Weakly alkaline powder detergent compositions were prepared according to the formulation shown in Table 12 and using the enzymes listed in Table 13.

The results of the evaluation of the detergent compositions are given in Table 13, which shows superior detergency of the detergent compositions of the present invention as compared to those containing conventional enzymes in removing naturally produced soil on collars.

Example 5

Weakly alkaline powder detergent compositions were prepared according to the formation shown in Table 14 and using the enzymes listed in Table 15.

The results of the evaluation of the detergent compositions are given in Table 15, which shows superior detergency of the detergent compositions of the present invention as compared to those containing conventional enzymes in removing naturally produced soil on collars.

TABLE 14

| Components | wt % |
| --- | --- |
| Sodium linear alkylbenzene sulfonate (LAS) | 12.5 |
| α-Sulfo-fatty acid ester (α-SFE, $C_{12}$-$C_{18}$) | 12.5 |
| Sodium α-olefin sulfonate (AOS, $C_{14}$-$C_{16}$) | 12.5 |
| Sodium hydrogenated tallow | 2.5 |
| Polyethylene glycol (Average M.W. = 12,000) | 1.5 |
| Sodium polyacrylate (Average M.W. = 8,000) | 1.5 |
| 4A-type Zeolite | 25 |
| Sodium silicate (JIS #2) | 10 |
| Sodium carbonate | 10 |
| Sodium sulfite (anhydrous) | 1 |
| Fluorescent dye | 0.2 |
| Glauber's salt | Balance |
| Water | 6 |
| Enzyme (See Table 15) | Prescribed Amounts * or 0 |
| Total | 100 |

*50 APU/kg for Compositions 5-(a) to 5-(e); and 1% for Compositions 5-(f) to 5-(h);

TABLE 15

| Composition No. | Enzyme | Detergency Index |
| --- | --- | --- |
| 5-0 (Standard Composition) | — | 100 |
| 5-(a) (Invention Composition) | (a) | 104 |
| 5-(b) (Invention Composition) | (b) | 104.5 |
| 5-(c) (Comparative Composition) | (c) | 105 |
| 5-(d) (Comparative Composition) | (d) | 101 |
| 5-(e) (Comparative Composition) | (e) | 101 |
| 5-(f) (Comparative Composition) | (f) | 101.5 |
| 5-(g) (Comparative Composition) | (g) | 101 |
| 5-(h) (Comparative Composition) | (h) | 100.5 |

Example 6

Weakly alkaline powder detergent compositions were prepared according to the formulation shown in Table 16 and using the enzymes listed in Table 17.

The results of the evaluation of the detergent compositions are given in Table 17, which shows superior detergency of the detergent compositions of the present invention as compared to those containing conventional enzymes in removing naturally produced soil on collars.

TABLE 16

| Components | wt % |
| --- | --- |
| Polyoxyethylene alkyl ether ($C_{12}$-$C_{14}$, EO = 7 mol) | 25 |
| Sodium hydrogenated tallow | 2.5 |
| Polyethylene glycol (Average M.W.-12,000) | 1.5 |
| Sodium polyacrylate (Average M.W. = 8,000) | 1.5 |
| 4A-type Zeolite | 40 |
| Sodium silicate (JIS #2) | 10 |
| Sodium carbonate | 10 |
| Sodium sulfite (anhydrous) | 1 |
| Fluorescent dye | 0.2 |
| Glauber's salt | Balance |
| Water | 5 |
| Enzyme (See Table 17) | Prescribed Amounts * or 0 |
| Total | 100 |

*50 APU/kg for Compositions 6-(a) to 6-(e); and 1% for Compositions 6-(f) to 6-(h);

TABLE 17

| Composition No. | Enzyme | Detergency Index |
| --- | --- | --- |
| 6-0 (Standard Composition) | — | 100 |
| 6-(a) (Invention Composition) | (a) | 105 |
| 6-(b) (Invention Composition) | (b) | 105 |
| 6-(c) (Comparative Composition) | (c) | 102 |
| 6-(d) (Comparative Composition) | (d) | 102 |
| 6-(e) (Comparative Composition) | (e) | 103 |
| 6-(f) (Comparative Composition) | (f) | 102 |
| 6-(g) (Comparative Composition) | (g) | 101.5 |
| 6-(h) (Comparative Composition) | (h) | 100.5 |

Example 7

Weakly alkaline liquid detergent compositions were prepared according to the formulation shown in Table 18. The detergent composition liquids had a pH of 9.6. The following enzymes were formulated in the compositions.

(i) Alkaline protease K-16 (the product obtained in Reference Example 2 diluted to a volume of 100-fold with glycerol and water).

(j) Alkaline protease K-14 (the product obtained in Reference Example 3 diluted to a volume of 100-fold with glycerol and water).

(k) Protease (a product of Novo Nordisk Co.; ESPERASE 8.0L ®)

(l) Protease (a product of Novo Nordisk Co.; SAVINASE 8.0L ®)

The results of the storage stability test conducted according to the following procedure are presented in Table 19.

Storage Stability Test

The compositions as produced were left at a temperature of 40° C., and the residual activity of enzyme in each composition after 10 days and 20 days were measured on samples diluted with tap water (Hardness: 2.5° HD) to a concentration of 1%, by subjecting them to AUTOANALYZER ® (trademark, manufactured by Technicon Co.), and the description in *Analyst*, 96(2), 159-163 (1971) was used for the details of the measurement. The residual activity of each enzyme was calculated according to the following equation.

Residual Enzyme Activity (%) =

$$\frac{\text{Enzyme Activity after 10 or 20 days}}{\text{Initial Enzyme Activity}} \times 100$$

TABLE 18

| Components | wt % |
| --- | --- |
| Sodium alkylethoxy sulfate ($C_{14}$-$C_{15}$, EO = 1.5 mol) | 25 |
| Secondary alcohol ethoxylate ($C_{13.5}$, EO = 7 mol) | 25 |
| Polyethylene glycol (Average M.W. = 6,000) | 2 |
| Fluorescent dye | 0.3 |
| Ethanol | 8 |
| Greenish flavoring agents | 0.05 |
| Water | Balance |
| Enzyme (See Table 19) | Prescribed Amounts * or 0 |
| Total | 100 |

*30 APU/kg for Compositions 7-(i) to 7-(l).

TABLE 19

| Composition No. | Enzyme | Residual Enzyme Activity | |
|---|---|---|---|
| | | After 10 days | After 20 days |
| 7-(i) (Invention Composition) | (i) | 95 | 80 |
| 7-(j) (Invention Composition) | (j) | 95 | 75 |
| 7-(k) (Comparative Composition) | (k) | 95 | 80 |
| 7-(l) (Comparative Composition) | (l) | 40 | 15 |

Obviously, numerous modifications and variations of the present invention are possible in light of the above teachings. It is therefore to be understood that, within the scope of the appended claims, the invention may be practiced otherwise than as specifically described herein.

What is claimed is:

1. A detergent composition, comprising:
   (a) an alkaline protease which has an activity of hydrolyzing human horny keratin fiber of 40 KFU/APU or more, and wherein said alkaline protease possesses the following optimum pH range and optimum temperature range;
   (1) optimum pH range when reacted at 40° C. using casein as a substrate: 10.0–12.5
   (2) optimum temperature range when reacted at pH 10.0 using casein as a substrate, with no $Ca^{+2}$ ions: 50°–60° C.; and
   (b) at least one component selected from the group consisting of surface active agents, divalent metal sequestering agents, inorganic salts, anti-redeposition agents, additional enzymes, effective chlorine capturing or reducing agents, bleaching agents, fluorescent dynes, solubilizing agents, perfumes, caking preventatives, enzyme activators, antioxidants, antiseptics, pigments, blueing agents, bleaching activators, and water, wherein said alkaline protease is present in an amount of 5–400 APU per 1 Kg of said composition.

2. A detergent composition according to claim 1, wherein said alkaline protease is alkaline protease K-16.

3. The detergent composition of claim 1, wherein said alkaline protease is alkaline proteinase K-14.

* * * * *